US006335191B1

(12) United States Patent
Kiplinger et al.

(10) Patent No.: US 6,335,191 B1
(45) Date of Patent: *Jan. 1, 2002

(54) AUTOMATED SYSTEM AND METHOD FOR GROWING BACTERIA

(75) Inventors: Dale Vilmer Kiplinger, Carrollton; Judith Gayle Pruitt, Mesquite; Jose Eduardo Evaro, Irving; Robert Clarence Pearce, III, Arlington, all of TX (US)

(73) Assignee: NCH Corporation, Irving, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/227,792

(22) Filed: Jan. 8, 1999

Related U.S. Application Data

(63) Continuation-in-part of application No. 09/031,642, filed on Feb. 27, 1998, now abandoned.

(51) Int. Cl.⁷ ............................ C02F 3/00; C12M 1/00; C12N 1/00; C12N 1/04; C12N 1/20
(52) U.S. Cl. ................. 435/252.1; 210/600; 210/601; 210/610; 435/243; 435/246; 435/260; 435/261; 435/283.1; 435/286.1; 435/289.1; 435/298.1; 435/308.1; 435/813; 435/818
(58) Field of Search .......................... 435/243, 281, 435/246, 252.1, 260, 261, 283.1, 286.1, 286.7, 289.1, 813, 818, 298.1, 308.1; 210/600, 601, 610

(56) References Cited

U.S. PATENT DOCUMENTS

| 1,618,461 A | | 2/1927 | Matchette ................. 435/286.6 |
|---|---|---|---|
| 3,152,983 A | | 10/1964 | Davis et al. ................. 210/611 |
| 3,220,706 A | | 11/1965 | Valdespino ................. 261/18.1 |
| 3,617,538 A | | 11/1971 | Bogert ........................ 210/612 |
| 3,642,257 A | | 2/1972 | Tanaka et al. ................. 261/93 |
| 3,854,700 A | * | 12/1974 | MacManus ..................... 259/4 |
| 4,051,204 A | | 9/1977 | Muller et al. ............... 261/36.1 |
| 4,244,815 A | | 1/1981 | Chaikin et al. ............. 210/622 |
| 4,260,490 A | * | 4/1981 | Moss et al. ................. 210/620 |
| 4,426,450 A | | 1/1984 | Donofrio .................... 435/243 |
| 4,576,616 A | * | 3/1986 | Mottram et al. ................ 55/68 |
| 4,797,208 A | | 1/1989 | Miller et al. ................. 210/606 |
| 4,832,848 A | | 5/1989 | Velebil et al. ............... 210/617 |
| 4,840,905 A | | 6/1989 | Kearns et al. ............... 435/394 |
| 4,883,759 A | | 11/1989 | Hopkins .................. 435/295.1 |
| 4,888,294 A | | 12/1989 | Van Wezel et al. ....... 435/297.3 |
| 4,911,832 A | | 3/1990 | Miller et al. .................. 210/86 |
| 4,925,564 A | | 5/1990 | Francis ........................ 210/608 |
| 4,960,706 A | | 10/1990 | Bliem et al. ............. 435/295.3 |
| 5,162,204 A | | 11/1992 | Matsuzaki et al. ............ 435/29 |
| 5,225,083 A | | 7/1993 | Pappas et al. ............... 210/606 |
| 5,369,032 A | | 11/1994 | Pratt ........................ 435/286.7 |
| 5,447,866 A | | 9/1995 | Runyon ...................... 435/289 |
| 5,654,197 A | | 8/1997 | Jem et al. .................... 435/383 |
| 6,012,383 A | * | 1/2000 | Lande' ....................... 99/453 |
| 6,027,449 A | * | 2/2000 | Mazess et al. ............... 600/449 |
| 6,099,735 A | * | 8/2000 | Kelada ........................ 210/652 |
| 6,213,007 B1 | * | 4/2001 | Lande .......................... 99/453 |

FOREIGN PATENT DOCUMENTS

| DE | 19507456 A1 | 9/1995 |
|---|---|---|
| EP | 0130499 A1 | 1/1985 |
| GB | 2162195 A | 1/1986 |
| JP | 403266974 | 11/1991 |

* cited by examiner

Primary Examiner—David M. Naff
Assistant Examiner—Deborah K. Ware
(74) Attorney, Agent, or Firm—Locke Liddell & Sapp LLP; Monty L. Ross

(57) ABSTRACT

An automated system and method is provided for cultivating bacteria in a fluid medium and thereafter selectively discharging the fluid medium, wherein an initial supply of the selected strain or strains of bacteria is combined with nutrients and water in a biogenerator in the presence of air to promote mixing and bacterial cultivation. The system and method utilize a vortex created by recirculation of the fluid medium to achieve aeration and mixing without substantial foaming. The system and method are particularly useful for supplying bacteria to control grease accumulation in restaurant grease traps. The system and method use a biogeneration chamber which has a cylindrical sidewall and surface on the inner side. Further, the chamber has a top and a conical bottom. The top has inlet ports and a vent port. There is also a outlet port in the conical bottom. The conical bottom also has a orifice and recirculated fluid inlet port that is directed tangentially along the inside surface of the sidewall to create a downwardly spiraling vortex in the biogeneration chamber.

31 Claims, 1 Drawing Sheet

AUTOMATED SYSTEM AND METHOD FOR GROWING BACTERIA

CROSS-REFERENCE TO RELATED APPLICATION

This application is a continuation-in-part of application Ser. No. 09/031,642, filed Feb. 27, 1998 now abandoned, which is incorporated by reference herein.

TECHNICAL FIELD

The present invention relates to bacteria cultivation and dispensing systems, and more particularly to an automatic bacteria cultivation and dispensing system that is useful for incubating bacteria from a starter population to a utility population within a predetermined interval and thereafter dispensing sufficient bacteria to perform a desired utility. A preferred utility for the disclosed system is the removal of grease from grease traps in commercial food preparation establishments.

BACKGROUND OF THE INVENTION

In the environment, bacteria are constantly working to naturally break down organic materials. This natural process generally causes some organic materials to eventually degrade into carbon dioxide and water. Under normal conditions, competition for resources, limited supplies of nutrients, and natural enemies can combine to inhibit rapid bacterial growth. By isolating selected strains of bacteria and providing a food source they prefer, bacteria can be made to multiply at a very fast rate. A large quantity of bacteria can be generated in this manner within a relatively short time. The bacteria can then be used in a wide variety of applications where the breakdown of organic materials is desirable.

One application where the breakdown of organic materials is particularly useful is in the maintenance of grease traps. Grease traps are required on virtually all commercial facilities that discard liquid or solid grease into a sewer system. Grease traps generally range from a capacity of about five gallons to over several thousand gallons. The majority of fast food kitchens are equipped with grease traps of about 1000 gallons. The system of drains used for grease traps is generally separate from the drains that carry away waste products from restrooms, spent drinking water, etc. Grease traps tend to collect not only oils and fats, but also various organic waste materials such as starches and vegetable waste products. Normally, a significant flow of wastewater is also introduced into the separate grease trap drainage system from kitchen drains where grease is often found. To prevent the wastewater from flushing grease into the city sewer system, grease traps are designed with a series of weirs that trap the grease within the containment vessel and allow wastewater to pass through the vessel on to a city treatment facility.

Inevitably, however, some of the grease in the grease trap passes into the city sewage system downstream from the restaurant. This does not create problems if the amount of grease passing into the sewer system is kept at a low level. Most city standards restrict the release of grease into sewer lines to approximately 250 ppm or less. If significant amounts of grease pass into the sewage system, the grease can cause blockages in the city pipes. When this occurs, the grease trap can overflow into the street, causing health problems. City maintenance crews often have to dig up the pipes under the street to remove the blockage. The cost of this procedure is typically passed on to the restaurant that released the grease. The restaurant usually must also pay a fine. For repeat offenders, the blockage can result in closure of the facility.

To avoid such problems, the current practice is to periodically collect the solid grease that floats on the top of the grease trap. In addition, every four to eight weeks, a service company should remove grease and other solid material that has settled and accumulated in the bottom of the grease trap, and should steam strip the walls and weirs. The cost of this service varies depending on the geographical region and the contract agreed upon by the restaurant owner and the service company, but is substantially greater over time than will be required using the system and method disclosed herein. If the grease trap is not pumped out on a regular basis, the grease layer can form such a thick crust that it blocks the inlet line into the grease trap and causes wastewater to back up into the facility. Such a back-up can require closing the restaurant or facility until the problem is resolved. Because of the potential fines and the possibility of temporary or permanent closure, maintenance of grease traps is of great importance to the owners of commercial food preparations establishments.

There are currently several products on the market that purportedly reduce the number of pump-outs needed. Many of these products are solvent-based or are detergents containing enzymes that will allegedly make the grease trap maintenance free. While many of these solvents or detergent products will dissolve the grease in the grease trap, the liquified grease often resolidifies a few feet down the sewage pipes, thereby blocking the flow of wastewater.

Another known device for treating grease traps uses bacteria in an attempt to digest the grease. The device includes a five gallon bucket that contains a bacterial gel material. Water continuously flows through the bucket and into the drain system. A disadvantage of this device is that most of the bacteria is introduced into the grease trap during periods of high kitchen activity. The volume of wastewater that flows through the grease trap flushes most of the bacteria through the grease trap and into the sewer system before the bacteria is able to digest the grease. In addition, a typical grease trap is generally a poor environment for growing bacteria rapidly due to a lack of oxygen, as well as the presence of contaminants such as detergents and antibacterial chemicals used in cleaning operations.

Another known treatment is to introduce preserved bacteria into the grease trap. This type of bacteria is generally in the form of a dry powder that consists of dormant bacteria spores. Before the growth of bacterial colonies can occur, these dormant spores must go through an incubation period to form active vegetative cells. This process takes about six hours to occur. If the spores are introduced into the grease trap before this time, most of the bacteria will be flushed from the grease trap before digestion can occur.

Another known method of maintaining a grease trap is to grow large quantities of active bacteria offsite using a filtered air supply, distilled water, and a specially designed growth chamber. The large amount of bacteria needed to sufficiently digest the grease in the grease trap, however, has not been affordable because large volumes of bacteria are expensive to produce and difficult to transport.

Applicants' copending application Ser. No. 09/031,642, filed Feb. 27, 1998, discloses an inexpensive and simple system and method for producing and dispensing large quantities of selected strains of bacteria into grease traps. That system and method are used to produce bacteria onsite in a favorable growth environment and to automatically dispense a predetermined volume of liquid containing active bacteria into the grease trap drain system during the night or at other times when flow through the trap is minimal. During use of that system, however, excessive foaming can occur in the biogeneration chamber even in the presence of an antifoaming agent due to the continuous introduction of air needed for bacterial growth through a tube having its discharge end submerged in the bacteria cultivation mixture. Such excessive foaming can cause the biogeneration chamber to overflow through the vent line, causing loss of nutrients, water and cell count, thereby slowing the desired bacterial growth.

Prior art devices said to be useful for aerating a cultivation medium within a tank, vessel or container to promote fermentation or bacterial growth are disclosed, for example, in U.S. Pat. Nos. 4,051,204; 4,426,450; 4,883,759; and 4,888,294.

SUMMARY OF THE INVENTION

The present invention comprises an automated biogeneration system and method for producing and dispensing liquid concentrates of active bacteria at predetermined intervals. According to a preferred embodiment of the invention, bacteria produced in this manner can be used to digest organic material in a grease trap and to reduce the frequency of pump-outs required. The system and method of the invention can also be used to supply bacteria for many other useful applications as disclosed below.

According to one preferred embodiment of the invention, a method for growing and selectively discharging bacteria is disclosed whereby water and a predetermined quantity of a powdered mixture of dehydrated "starter" bacteria and appropriate nutrient(s) are automatically introduced into a biogeneration chamber for the purpose of growing and quickly multiplying the selected bacteria. Multiple strains of bacteria can be used as long as the nutrient package is designed to support each of the multiple strains. Pressurized air is supplied to the chamber to support aerobic bacterial reproduction, and is desirably introduced according to a special method using a vortex that controls foaming within the biogeneration chamber. After the mixture is placed in the biogeneration chamber, the bacteria are permitted to grow and reproduce for a desired time, such as about 24 hours, while continually withdrawing liquid from the bottom of the chamber, recirculating it with a pump, and reintroducing it into the chamber in a tangentially directed flow to create the desired vortex. At the end of the growing period, the active bacteria are preferably discharged from the biogeneration chamber to another holding vessel or, more preferably, directly to a use site such as a restaurant grease trap. Once the contents of the biogeneration chamber are discharged, the process is repeated. The cycle of operation is desirably controlled by an electronic timer having relays that activate and deactivate switches and valves in accordance with predetermined parameters. Significant increases in bacterial production are observed using the system and method disclosed herein as compared to applicants' previously disclosed system and method.

According to another preferred embodiment of the invention, an automated batch system for growing and selectively discharging a bacteria-containing fluid is disclosed that comprises a biogeneration chamber having a substantially cylindrical sidewall, a top and a conical bottom, a feed source communicating with a feed inlet port in the top, a water source communicating with a water inlet port in the top, a pressurized air source communicating with an air inlet port in the top, a vent line communicating with a vent port in the top, a centrally disposed outlet port in the conical bottom, an orifice element disposed in the conical bottom at or near the outlet port, a recirculated fluid inlet port positioned and directed so as to reintroduce recirculated fluid into the chamber in a substantially tangential direction relative to the inside wall, a recirculating pump, flow tubing placing the recirculating pump inlet in fluid communication with the chamber outlet port and placing the recirculating pump outlet in fluid communication with the recirculated fluid inlet port, and a valve disposed in the flow tubing between the recirculating pump and the recirculated fluid inlet port to selectively divert flow from the pump to a drain line also communicating through the pump and the valve with the chamber outlet port.

BRIEF DESCRIPTION OF THE DRAWINGS

The preferred embodiments of the invention are further described with reference to the accompanying drawings wherein.

DESCRIPTION OF THE PREFERRED EMBODIMENT

The automated biogeneration system and method of the present invention are useful for rapidly growing a relatively large supply of selected strains of bacteria using a relatively small quantity of starter bacteria. The method of the invention provides a low maintenance, hands-free process for growing bacteria that, depending upon the bacterial strains selected, are useful in a variety of applications. Although other possible applications for the system and method disclosed herein are discussed below, a particularly preferred application is the cultivation of bacteria for use in digesting grease in grease traps such as those used in the restaurant industry. If a large enough supply of suitable, active bacteria can be introduced into a grease trap on a frequent basis, the grease accumulation inside the trap can be controlled at levels that permit less frequent pump-outs and steam cleaning of the type now regularly required. This reduces service fees and facilitates compliance with regulations governing the amount of grease that can be released into municipal sewer systems.

In accordance with a preferred embodiment of the invention, an automatic system and method are disclosed for creating large batches of active bacteria that thrive on grease and other organic matter, such as starches, sugars, and proteins. The automated function reduces labor costs, and the biogeneration chamber provides a favorable environment for growing bacteria. When introduced into a grease trap, generally through a drain line downstream of the P-trap, the large volume of bacteria produced digests some of the organic materials in the grease trap, producing carbon dioxide and water as the principal waste products.

The starter bacteria and nutrients needed to support growth and reproduction of the bacteria within the biogeneration chamber are easily transported, most preferably in powder form, making the transport of large supplies of bacteria unnecessary. The subject method does not require precise control of the temperature; nor is it necessary to use a filtered air supply or distilled water. Because multiple strains of desirable bacteria can be grown simultaneously in the same biogeneration chamber, they are capable of digesting a variety of organic materials found in grease traps while simultaneously reducing odor problems. Because they are grown onsite, the useful bacteria are active upon introduction into a grease trap. Furthermore, by introducing the bacteria during periods of low kitchen activity, the bacteria's residence time in the grease trap can be maximized.

Figure 1:
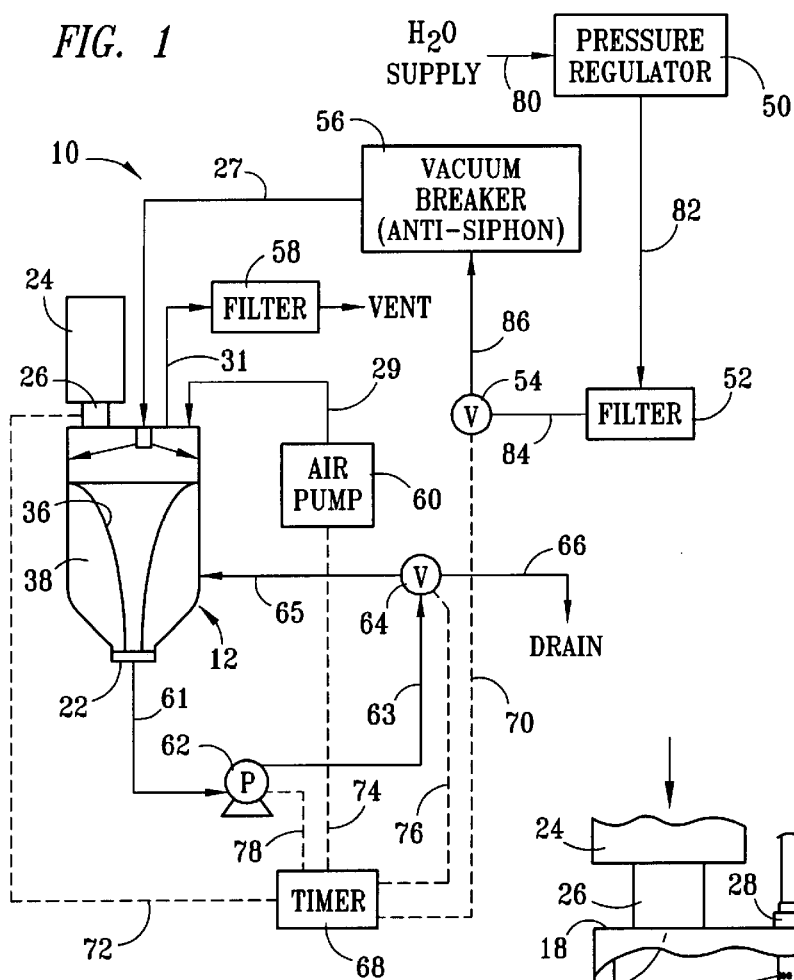
FIG. 1 is a simplified schematic view of a biogeneration system made in accordance with the present invention.

Referring to FIG. 1, system 10 of the invention preferably comprises biogeneration chamber 12, a feed source 24 of starter bacteria and nutrients, a feed control device 26, a water supply, a pressurized air supply, fluid recirculation pump 62, solenoid valves 54 and 64, timer 68, flow conduits 27, 29, 31, 61, 63, 65, 66, 82, 84 and 86, and control lines 70, 72, 74, 76 and 78 respectively linking timer 68 to valves 54 and 64, air pump 60, feed control device 26 and fluid recirculation pump 62. The water supply is preferably fresh potable water provided to biogeneration chamber 12 at ambient temperature through flow line 80, pressure regulator 50, flow line 82, filter 52, flow line 84, water inlet solenoid valve 54, anti-siphon vacuum breaker 56 and flow line 27. The pressurized air supply is preferably an air pump 60, such as an aquarium air pump, capable of delivering to biogeneration chamber 12 a sufficient supply of air to support rapid bacterial growth at a pressure sufficient to enter the biogeneration chamber without disrupting the vortex 36 created therein as discussed below. The required air flow will of course vary according to the volume of biogeneration chamber 12 and the volume of the bacteria-containing fluid mixture 38 within the chamber. Vent line 31 is provided to prevent pressure build-up inside biogeneration chamber 12 and is preferably filtered by filter 58, and exhausted to atmosphere or some other type of recovery unit as desired or that may be required under special circumstances. Vent line 31 can be connected to an existing drain system downstream from the P-trap to allow venting of biogeneration chamber 12 without releasing bacteria into the kitchen area. If connected to a drain, vent line 31 can also comprise a conventional diaphragm check valve or backflow preventer (not shown in FIG. 1) to prevent unwanted bacteria from entering the biogeneration chamber 12 from the drain. useful for the intended application and nutrients needed for the starter bacteria to grow and replicate rapidly within biogeneration chamber 12. According to a particularly preferred embodiment of the invention, the starter bacteria and nutrients are provided together in a premixed powder that is activated when hydrated and mixed in the presence of air. While the use of a dry, premixed powder feed is preferred, liquid feeds can also be used in the subject system and method, and the nutrients do not necessarily have to be premixed with the starter bacteria. Feed control device 26 can be any device or combination of devices suitable for introducing starter bacteria and nutrients into biogeneration system 12 in a controlled manner and can include, for example, a rotary valve, sliding volumetric gate, vibrating roller mechanism, weigh-belt conveyor, or the like. Alternatively, premixed powder can also be aspirated into the water inlet line using a venturi arrangement. Although a single feed source 24 and feed control device 26 are depicted in FIG. 1, it is understood that a plurality of such feed sources and/or feed control devices can also be used within the scope of the invention.

Fluid recirculation pump 62 withdraws fluid mixture 38 from biogeneration chamber 12 through outlet port 22 and line 61, and depending upon the setting of three-way solenoid valve 64, either returns the fluid mixture to biogeneration chamber 12 through lines 63 and 65 or else discharges the fluid mixture to a drain or other receptacle through lines 63 and 66. Fluid recirculation pump 62 is desirably a centrifugal pump, although it is understood that diaphragm pumps and other similarly effective fluid recirculation devices can also be used within the scope of the invention. Diaphragm pumps are self-priming and are less affected by excess air in the fluid mixture. Fluid recirculation pump 62 is depicted in FIG. 1 as being controlled by timer 68, but it is understood that pump 62 can also be controlled, for example, by electrical, mechanical, optical or ultrasonic level indicators or sensors in biogeneration chamber 12 and related switches as needed.

Timer 68 is desirably a conventional electronic control device capable of timing multiple events in the cycle of operation and signaling switches in feed control device 26, air pump 60, solenoid valves 54 and 64, and fluid recirculation pump 62 in accordance with the method of the invention as described below. It will appreciated upon reading this disclosure, however, that some or all of the control functions performed by timer 68 can also be performed within the scope of the invention by the use of multiple timers, a program logic controller, a custom designed programmable circuit board, a PC based controller, pneumatic controllers, level controllers and other similarly effective means. Timer 68 will desirably accept and react to inputs from conductivity sensors, mechanical floats, optical sensors, ultrasonic sensors, and the like, and may also be capable of simultaneously operating other equipment or apparatus, whether or not depicted in FIG. 1 or described herein.

Figure 2:
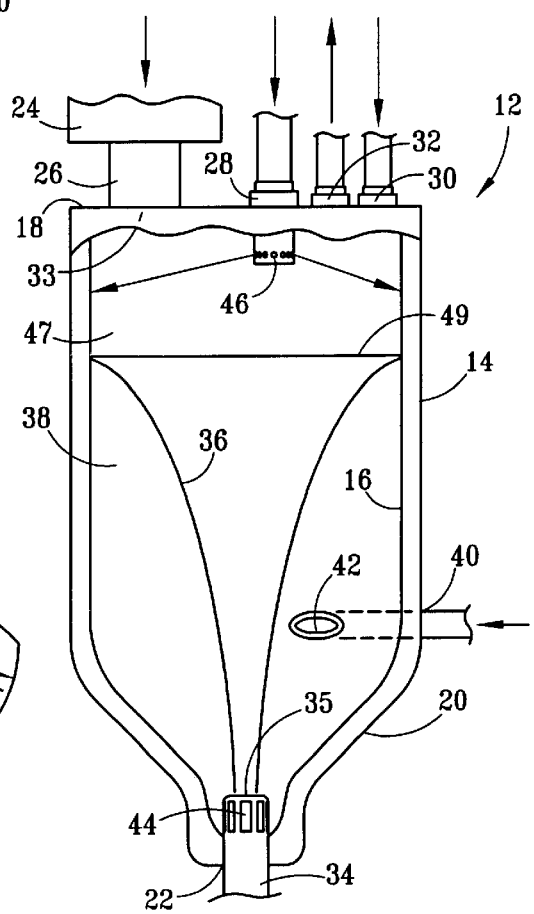
FIG. 2 is an enlarged, simplified front elevation view of the biogeneration chamber shown in FIG. 1.

A preferred biogeneration chamber 12 for use in system 10 and the method of the invention is further described and explained in relation to FIG. 2. Biogeneration chamber 12 preferably comprises a substantially cylindrical sidewall 14 with interior surface 16 that is smoothly and continuously joined to a conical lower section 20 having a centrally disposed chamber outlet port 22 at its lower end. Top 18 may be flat, domed or otherwise shaped, and is desirably removable to permit periodic cleaning of inside surface 16 of biogeneration chamber 12. Water inlet port 28, air inlet port 30, feed inlet port 33 and vent port 32 are desirably provided in top 18 to communicate with water inlet line 27, air inlet line 29, feed control device 26 and vent line 31, respectively. Disperser nozzle 46 is preferably provided in water inlet port 28 to direct water introduced into biogeneration chamber 12 in a 360° spray against interior surface 16, and can also function as a rinse nozzle during clean-out of chamber 12 if desired. Orifice element 34 is preferably provided in chamber outlet port 22 to assist in controlling the amount of air entering line 61 (FIG. 1) from vortex 36 in fluid medium or mixture 38. Too great a restriction in orifice element 34 can starve fluid recirculation pump 62 and promote plugging of the orifices.

Applicants have discovered that vortex 36 within biogeneration chamber 12 is an effective tool for mixing the bacteria and nutrients in the fluid medium and for aerating fluid mixture 38 without causing the significant amount of undesirable foam that is produced in prior art systems when air is bubbled into a biogenerator beneath the surface of a fluid mixture. The amount of aeration achieved with vortex 36 also significantly surpasses the aeration achieved when air is introduced above the fluid surface without a vortex. Vortex 36 is preferably created by the continuous reintroduction into biogeneration chamber 12 of a portion of fluid mixture 38 that is withdrawn through outlet port 22 and recirculated by pump 62 through line 63, valve 64 and line 65 to recirculated fluid outlet port 42 disposed closely adjacent to interior surface 16, most preferably above conical section 20. Port 42 preferably communicates with the interior of biogeneration chamber 12 in a direction and in such manner that a continuous stream of recirculated fluid mixture 38 is reintroduced into biogeneration chamber 12 and directed horizontally along interior surface 16 in a direction that is characterized herein as being "substantially tangential" to interior surface 16. Although the term "tangential" ordinarily refers to a line tangent to a point on the circumference of a circle or cylinder that is directed away from the curve, the term is used herein to describe a curved flowpath, initially established in a substantially horizontal direction around inside surface 16 of biogeneration chamber 12, that diverges from horizontal as it continues around interior surface 16 and creates a downwardly spiraling vortex 36 in the center of biogeneration chamber 12. Port 42 can be disposed in a nozzle built into sidewall 14 of biogeneration chamber 12 or can be disposed at the end of a line extending interiorly past interior surface 16 as shown in FIG. 2. Although port 42 is shown as being elliptical in shape in FIG. 2, it will be understood that other shapes can also be used within the scope of the invention.

Orifice element 34 as shown in FIG. 2 is a cylindrical body having a top with a smaller-diameter orifice 35 and a plurality of rectangular, slot-like orifices 44 circumferentially spaced around its perimeter. It is to be understood that other orifice configurations can also be used within the scope of the present invention. As discussed below in relation to the method of the invention, orifice element 34 is useful for permitting fluid mixture 38 to be drawn into and through chamber outlet port 22 without permitting vortex 36 to continue downwardly into and through outlet port 22, which could promote cavitation on the inlet side of fluid recirculation pump 62.

Figure 3:
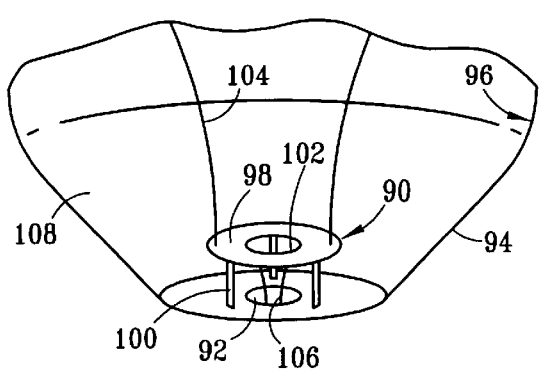
FIG. 3 is an enlarged, simplified front perspective view, partially broken away, depicting one orifice element as installed in the bottom of a biogeneration chamber for use in the apparatus and method of the invention.

FIG. 3 discloses an alternative structure for an orifice element 90 disposed adjacent to chamber outlet port 92 inside conical section 94 of an otherwise similar biogeneration chamber 96. Orifice element 90 further comprises a disc 98 supported by legs 100 over outlet port 92, and has a smaller diameter, centrally disposed aperture 102. Disc 98 desirably has a diameter greater than that of outlet port 92 and supports vortex 104 slightly above outlet port 92, permitting fluid mixture 108 to be drawn into outlet port 92 around and beneath disc 98, where a smaller diameter vortex 106 is created that is less likely to cause surging, or cavitation of a fluid recirculation pump.

While the components of the invention will understandably be sized, configured and constructed according to the intended manner and place of use, satisfactory results are achieved using a one gallon bioreactor chamber 12 with a conical bottom as discussed below, a fill level within the chamber corresponding to a fluid volume ranging from about 1.5 to about 3 liters, a fluid recirculation pump 62 rated at about 3 gallons per minute, and a 50 micron inlet water filter 52. According to a particularly preferred embodiment of system 10 of the invention for use in a typical restaurant environment to generate bacteria for discharge into a grease trap, the system components as described above can be mounted inside a cabinet and locked to prohibit access except by authorized personnel. During normal operation, infrequent access to the system is needed in order to periodically replenish the starter bacteria and nutrients. Although the time for replenishing starter bacteria and nutrients will vary according to the volume of feed source 24 and the volume of biogeneration chamber 12, monthly replenishment should be achievable in most instances. Infrequent removal and cleaning of biogeneration chamber 12 may also be desirable following a specified number of cycles of operation, which is also anticipated to be no more often than about once a month.

According to a preferred method of the invention, described herein in relation to FIGS. 1 and 2, a dry powder containing selected bacteria cultures and dry nutrients such as sugar, refined milk protein, corn starch, and bran is loaded into feed source 24. Desirable starter bacteria for controlling grease in a grease trap preferably include bacillus, pseudomonas, enterobacter and mixtures thereof These organisms are known to digest various types of organic waste products that are commonly found in grease traps. Preferably, the starter bacteria is stabilized with a preservative and is inactive until it is diluted with water.

At the system start-up, timer 68 activates water solenoid valve 54, causing water to enter biogeneration chamber 12 through inlet port 28. After passing through vacuum breaker 56, which prevents fluid from chamber 12 from being siphoned back into the potable water system, water is sprayed into the biogeneration chamber, preferably a polyethylene container, through nozzle 46. Water flow is continued for a predetermined time or until fluid level 49 reaches a desired point, at which time valve 54 is closed to stop the flow. Timer 68 activates feed control device 26 to dispense a predetermined quantity of powder containing starter bacteria and nutrients into biogeneration chamber 12 through suitably sized inlet port 33, thereby hydrating and activating the starter bacteria. Air pump 60 is also activated by timer 68 and the slight positive pressure inside biogeneration chamber 12 effectively prevents unwanted bacteria from entering the biogeneration chamber after the initial start-up. Air pump 60 pumps fresh air into headspace 47 above liquid level 49, making air readily available for vortex 36 to siphon into fluid recirculating pump 62. The introduction of air into headspace 47 also helps carry off any gases created by the bacteria out through vent line 31. Although some unwanted bacteria may be introduced through the air supply or water supply, growth of unwanted organisms in relatively small numbers is not usually seriously detrimental to the process and can sometimes be suppressed by carefully selecting nutrients preferred by the desired bacteria.

Once the biogeneration chamber 102 is charged with water, starter bacteria, nutrients and air, fluid recirculation pump 62 is activated, and cultivation of the selected bacteria begins. Fluid recirculation pump 62 continuously draws a stream of fluid mixture 38 from conical bottom 20 of biogeneration chamber 12, through orifice element 34 in outlet port 22 and line 61, to the inlet side of the pump. Fluid circulation pump 62 discharges the pressurized fluid mixture 38 into line 63, and through three-way valve 64, which is automatically set to return fluid mixture 38 through line 65 to inlet port 42. As fluid mixture 38 is expelled from inlet port 42, fluid mixture 38 is cause to swirl inside chamber 12, desirably creating vortex 36 when the recirculation rate is properly adjusted, as for example, by controlling the pumping rate of pump 62.

When properly adjusted in order to promote mixing and aeration, the bottom of vortex 36 will desirably extend downward to orifice element 34 in outlet port 22. Orifice element 34 preferably prevents too much air or too little fluid mixture from entering line 61. Too much air can damage the rotor of a centrifuigal pump and, if excessive, stall the pump. Some cavitation at pump 62 may be desirable for mixing and aeration, and partial cavitation at the pump inlet can beat air into the liquid, producing a thick froth. So long as it does not overfill biogenerator chamber 12, some amount of foam can be desirable, increasing aeration, and also increasing the available surface area. With the present system and method, any excess foam that is created is drawn back into vortex 36 within chamber 12 and reinjected into fluid mixture 38. The ratio of air to liquid entering line 61 can be adjusted by modifying the orifice element 34 or the recirculation rate through pump 62. Through use of the present system and method, vortex 36 in conjunction with fluid recirculation pump 62 provides excellent mixing, aeration and foam control.

After bacterial cultivation has continued for a desired period, timer 68 or another similarly effective means causes three-way valve 64 to redirect the flow of fluid mixture 38 discharged by fluid recirculation pump 62 into drain line 66, which can be directed to a use site or to an intermediate storage vessel. Once fluid level 49 has been pumped down to a desired point, pump 62 is deactivated and valve 64 is returned to its former position. Valve 54 is then reopened and the cycle of operation is repeated.

Although application of the invention to treat grease in a grease trap is one preferred embodiment, the invention can be equally useful in a number of other applications where large quantities of bacteria are needed. The following list includes several other illustrative examples where the invention can be used:

(1) Growing bacteria for breaking down manure and urine in cattle barns and feed lots. Use of bacteria in this manner results in a digested material that can be put directly on fields for use as a fertilizer. The pre-digestion of manure and urine allows the fertilizers and nutrients to be released into the soil much faster and with less odor problems than handling the waste material in raw form.

(2) Bacterial decomposition of agricultural waste products such as sugar cane stalks and corn stalks that are slow to degrade when left in the fields.

(3) The biological treatment of oil spills. Such treatment has generally been very expensive because of the high cost of producing live bacteria. The present invention, if used in a larger, scaled-up version, can provide a cost-effective method of growing the necessary live bacteria onsite in quantities sufficient to quickly reduce the damage to the environment.

(4) Converting PCB's created by waste materials from transformer cooling oils into less harmful substances that can be further treated. This conversion reduces the environmental problems associated with current disposal practices. Treatment of these hazardous materials is currently very expensive.

(5) Use of bacteria to accelerate the decomposition of human waste as found in portable rest rooms and in septic systems.

(6) Use of bacteria to feed on algae that forms on cooling towers and in ponds and fountains. This use would reduce the need for the use of heavily regulated toxic chemicals.

(7) Using live bacteria to control insects that infest fruit and vegetable crops, aiding in insect and disease control.

(8) Using live bacteria to control fungi in turf for golf courses, on lawns, and in other plant life. In this application, the liquid bacteria mixture could be applied directly into the irrigation system. The addition of fertilizers to the mixture would also enhance the growth of the bacteria.

(9) Treatment of soil after underground oil or gas spills have occurred. The live bacteria or other organisms could be used to more efficiently treat an oil or chemical spill area than relying on the natural bacteria in the soil to degrade the spill.

(10) Production of active yeast products for commercial bakeries.

(11) Production of yeasts used in the fermentation and production of alcohol-related products.

(12) Decomposition of industrial organic waste products before being discharged down the drains. Food and bottling plants are often assessed large fines for discharging large amounts of fats, oils, starches, and sugar-based products in excess of permissible discharge levels. The system of the present invention can be used to digest such waste products.

While the system, apparatus and method of the invention are disclosed herein in relation to their preferred embodiments, other alterations and modifications of the invention will become apparent to those of ordinary skill in the art upon reading this disclosure, and it is intended that the invention disclosed herein be limited only by the broadest interpretation of the appended claims to which the inventors are legally entitled. Those skilled in the art will also recognize upon reading this disclosure that the physical size, placement and types of bacteria, nutrient, water and air supply devices, control devices, containers and pumps can be varied or modified within the scope of the invention to meet the needs of a particular application.

We claim:

1. An automated system useful for growing bacteria from a starter population within a predetermined interval and thereafter dispensing the bacteria to perform a utility, the system comprising:

a biogeneration chamber having a substantially cylindrical sidewall with an inside surface, a top and a generally conical bottom; the top further comprising feed, water and air inlet ports and a vent port; a centrally disposed chamber outlet port in the conical bottom; an orifice element disposed inside the conical bottom near the outlet port; and a recirculated fluid inlet port in the sidewall at a point slightly above the conical bottom, the recirculated fluid inlet port being directed substantially tangentially along the inside surface of the sidewall so as to create a downwardly spiraling vortex in the center of the biogeneration chamber whenever a recirculated fluid is discharged therefrom;

at least one timer;

at least one bacteria and nutrient feed source communicating with the feed inlet port, said source being controllable by said at least one timer;

a water source communicating with the water inlet port through a valve that is controllable by said at least one timer;

a pressurized air supply communicating with the air inlet port, the pressurized air supply being controllable by said at least one timer;

a vent line communicating with the vent port;

a recirculating pump having an inlet communicating with the chamber outlet port and an outlet communicating with the recirculated fluid inlet port; and a valve disposed between the recirculating pump and the recirculated fluid inlet port that is controllable by said timer to divert flow from the recirculating pump to a drain line that also communicates selectively with the chamber outlet port through the valve and the recirculating pump.

2. The automated system of claim 1 wherein the bacteria and nutrient feed source communicates with the feed inlet port through a dispensing apparatus.

3. The automated system of claim 1 wherein the dispensing apparatus is a valve controlled by the at least one timer.

4. The automated system of claim 1 wherein the dispensing apparatus is a conveyor controlled by the at least one timer.

5. The automated system of claim 1 comprising independently controllable bacteria and nutrient feed sources.

6. The automated system of claim 1 wherein the water supply is filtered and pressure regulated.

7. The automated system of claim 1 wherein the pressurized air supply is an aquarium air pump.

8. The automated system of claim 1 wherein the orifice element is a horizontally disposed orifice plate vertically separated a slight distance above the chamber outlet port.

9. The automated system of claim 8 wherein the orifice plate has an outside diameter greater than the diameter of the chamber outlet port and comprises a single orifice having a diameter smaller than the diameter of the chamber outlet port.

10. The automated system of claim 1 wherein the orifice element is a cylindrical structure having a diameter approximately equal to the diameter of the chamber outlet port and comprises a plurality of orifices disposed on its periphery that provide fluid communication between the interior of the chamber and the chamber outlet port.

11. The automated system of claim 1 wherein the recirculating pump is a centrifugal pump.

12. The automated system of claim 1 wherein the recirculating pump is a diaphragm pump.

13. An automated method for growing bacteria from a starter population within a predetermined interval and thereafter dispensing the bacteria to perform a utility, comprising the steps of:

introducing predetermined quantities of water, starter bacteria and nutrient into a substantially cylindrical biogenerator chamber having an interior with a generally conical bottom section to form a bacteria-containing fluid mixture;

introducing a stream of pressurized air into the chamber above the level of the fluid mixture inside the chamber;

continuously withdrawing a portion of the fluidized mixture through an orifice element disposed over an outlet port in the conical bottom section using a pump disposed downstream of the outlet port;

recirculating the withdrawn portion and reintroducing said portion substantially tangentially into the chamber to establish a downwardly spiraling vortex in the fluid mixture inside the chamber, said orifice element controlling the amount of air entering the pump from the vortex;

continuing the recirculation and the stream of pressurized air for a predetermined time sufficient to grow the bacteria while controlling any amount of foam in the biogenerator chamber so that any such foam does not overfill the biogenerator chamber; and discharging the fluid mixture from the chamber for use in the utility.

14. The method of claim 13 wherein the starter bacteria comprises at least one bacterial strain selected from the group consisting of bacillus, pseudomonas, enterobacter and mixtures thereof.

15. The method of claim 13 wherein the vortex is established by withdrawing the recirculated portion of the fluid mixture from the outlet port in the bottom of the chamber and reintroducing the recirculated portion into the chamber at a point above the conical section in a direction substantially tangential to the interior of the cylindrical chamber.

16. The method of claim 15 where in the recirculation rate is controlled to establish the vortex inside the chamber without cavitating the pump.

17. The method of claim 15 wherein the orifice element is provided adjacent to the outlet port to control the vortex so as to partially cavitate the pump.

18. The method of claim 13 wherein the fluid mixture is discharged from the chamber by selectively diverting the flow of fluid mixture withdrawn from the chamber outlet port rather than recirculating the fluid mixture to the chamber.

19. The method of claim 13 wherein the flow of pressurized air into the chamber is terminated prior to discharging the fluid mixture from the chamber.

20. The method of claim 13 wherein recirculation is continued for about a day prior to discharging the fluid mixture from the chamber.

21. The method of claim 13 wherein the utility is the digestion of grease in a grease trap.

22. The method of claim 13 wherein the utility is decomposition of animal waste.

23. The method of claim 13 wherein the utility is decomposition of plant waste.

24. The method of claim 13 wherein the utility is treatment of spills of oil and chemicals.

25. The method of claim 13 wherein the utility is conversion of PCB compounds into less harmful substances.

26. The method of claim 13 wherein the utility is the digestion of algae.

27. The method of claim 13 wherein the utility is the control of insect populations.

28. The method of cl aim 13 wherein the utility is the control of fungi in turf grasses.

29. The method of claim 13 wherein the utility is the production of active yeast products.

30. The method of claim 13 wherein the utility is the decomposition of industrial organic waste.

31. Apparatus for growing bacteria from a starter population and thereafter dispensing the bacteria to a storage vessel or use site, the apparatus comprising:

a biogeneration chamber having a substantially cylindrical sidewall with an inside surface, a top and a generally conical bottom, the top further comprising feed, water and air inlet ports and a vent port; a centrally disposed chamber outlet port in the generally conical bottom; an orifice element disposed adjacent to the chamber outlet port and functioning as a vortex breaker; and a recirculated fluid inlet port directed substantially tangentially along the inside surface of the sidewall;

a pressurized air supply communicating with the air inlet port;

a recirculating pump having an inlet communicating with the chamber outlet port and an outlet communicating with the recirculated fluid inlet port; and a valve disposed between the recirculating pump and the recirculated fluid inlet port that is controllable to divert a fluid flow from the recirculating pump to a drain line that also communicates selectively with the chamber outlet port through the valve and the recirculating pump.

* * * * *

UNITED STATES PATENT AND TRADEMARK OFFICE
CERTIFICATE OF CORRECTION

PATENT NO.   : 6,335,191 B1
DATED        : January 1, 2002
INVENTOR(S)  : Kiplinger et al.

It is certified that error appears in the above-identified patent and that said Letters Patent is hereby corrected as shown below:

Column 1,
Line 44, between "drain." and "useful" insert -- Feed source 24 is desirably a hopper or other container capable of maintaining and controllably releasing through feed control device 26 a mixture of starter bacteria --

Column 6,
Line 40, replace "o r" with -- or --.
Line 40, replace "s h aped" with -- shaped --.

Signed and Sealed this

Fourth Day of February, 2003

JAMES E. ROGAN
*Director of the United States Patent and Trademark Office*